(12) United States Patent
Gudapakkam et al.

(10) Patent No.: US 7,334,160 B2
(45) Date of Patent: Feb. 19, 2008

(54) METHOD AND APPARATUS FOR MANAGING A DISTRIBUTED X-RAY SYSTEM

(75) Inventors: Lakshmi Narayanan Gudapakkam, Waukesha, WI (US); Eswar Chandra Lingam, Waukesha, WI (US); Dalesh Somchand Dharamshi, Karnataka (IN); Medhi Venon, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1154 days.

(21) Appl. No.: 10/044,140

(22) Filed: Jan. 11, 2002

(65) Prior Publication Data

US 2003/0135389 A1  Jul. 17, 2003

(51) Int. Cl.
*G06F 11/00* (2006.01)
(52) U.S. Cl. .......................... 714/31; 714/25; 709/223
(58) Field of Classification Search ................... 714/31
See application file for complete search history.

(56) References Cited

U.S. PATENT DOCUMENTS

| | | | |
|---|---|---|---|
| 4,627,055 A * | 12/1986 | Mori et al. ................. | 714/11 |
| 5,664,093 A * | 9/1997 | Barnett et al. .............. | 714/31 |
| 5,787,246 A * | 7/1998 | Lichtman et al. ........... | 709/220 |
| 5,857,190 A * | 1/1999 | Brown ........................ | 707/10 |
| 6,175,934 B1 * | 1/2001 | Hershey et al. ............. | 714/25 |
| 6,243,835 B1 * | 6/2001 | Enokido et al. ............. | 714/38 |
| 6,460,070 B1 * | 10/2002 | Turek et al. ................ | 709/202 |
| 6,856,825 B2 * | 2/2005 | Hahn .......................... | 600/425 |
| 6,871,299 B2 * | 3/2005 | Havekost et al. ............ | 714/47 |
| 6,990,574 B2 * | 1/2006 | Bidarahalli et al. .......... | 713/2 |

OTHER PUBLICATIONS

GE Research and Development Center, From InSite to OnSite: Leveraging Technology for Rapid Service Growth, Sep. 8, 1997, Post, No. 1648, pp. 1-2.*

* cited by examiner

*Primary Examiner*—Scott Baderman
*Assistant Examiner*—Paul F Contino
(74) *Attorney, Agent, or Firm*—McAndrews, Held & Malloy, Ltd.; Peter J. Vogel; Michael A. Dellapenna (57) ABSTRACT

A preferred embodiment of the present invention provides a method and system for managing a distributed medical diagnostic imaging system. The system includes a system manager for managing the medical diagnostic imaging system, a subsystem that includes a subsystem manager for managing the subsystem and an actor, or task operator, capable of executing certain functions. The subsystem manager reports to the system manager. The system also includes a communication channel for transmitting data between the system manager and the subsystem. The system may include a plurality of subsystems with a plurality of actors or task operators. The components of the system may be configured and adjusted.

20 Claims, 5 Drawing Sheets

MaxBootLevels = 2;
No. of subsystems = 3;
Subsystems for level 1 =
{A,B}
Subsystems for level 2 =
{A,B,C}
.
.
.

220

MaxBootLevels = 2;
No. of actors = n;
Actors for level 1 =
{w,x}
Actors for level 2 =
{w,x,y,z}
Actors for Diagnostics =
{w,y}
.

METHOD AND APPARATUS FOR MANAGING A DISTRIBUTED X-RAY SYSTEM

BACKGROUND OF THE INVENTION

Certain embodiments of the present invention generally relate to distributed medical diagnostic imaging systems, and in particular, relate to generic systems management of a distributed medical diagnostic imaging system.

Medical diagnostic imaging systems, such as x-ray systems, ultrasound systems, computed tomography systems, or other imaging systems, have been proposed that are configured according to a master-slave architecture. In a master-slave architecture, a master computer controls operation of the overall imaging system and slave computers execute commands from the master computer and report the results of such execution, including successes and failures, back to the master computer. Control of the imaging system is centralized in a two-tier master-slave model with the master computer performing all system control operations.

In current medical diagnostic imaging systems, a single entity or master, such as a single processor or control unit, for example, manages the imaging system and subsystems. The master is typically constructed or configured for the particular imaging system and components of that imaging system. However, subsystems may include different hardware with a difference in behavior from other subsystems. Thus, when the architecture of an imaging system is altered, the master is altered as well. Therefore, since the master is altered or replaced when the composition of the imaging system is altered, the system is not easily scalable or alterable. Thus, a need exists for a medical diagnostic imaging system with a control system that is easily adjustable and scalable.

Further, in conventional master-slave architectures, when a problem or error arises in a medical diagnostic imaging system, the imaging system may have difficulty in locating and correcting the error, since an error may be located anywhere from the master down to any of the slave components in the imaging system. That is, typically, the master is unable to locate in which system component an error has occurred and has little detail regarding the error. For example, in a master-slave x-ray system, the master transmits a system command to the slave components of the x-ray system. An error may be discovered if the system does not function properly, but a human operator would not be able to determine whether the error occurred in the master or in any one of the slave components without more extensive diagnostics because component communication is lacking in a typical master-slave x-ray system.

Also, medical diagnostic imaging systems with a master-slave architecture experience more failures than stand-alone imaging systems because minor problems may remain undetected until developing into significant problems or until compounded by separate significant problems. Furthermore, the status of underlying components may not be regularly monitored in a master-slave imaging system because the master simply transmits commands to the slave components and may not receive detailed status reports from slave components and subsystems.

Thus, there is a need for improved control and coordination of a medical diagnostic imaging system in order to better monitor system status. There is a need for improved management of a medical diagnostic imaging system outside the master-slave architecture. There is also a need for a medical diagnostic imaging system with a control system that is easily adjustable and scalable. There is a further need for a medical diagnostic imaging system with a reduced failure rate due to improved system coordination and control. There is also a need for an improved method of detecting system errors in a medical diagnostic imaging system through improved system coordination and control to localize and locate errors.

BRIEF SUMMARY OF THE INVENTION

Certain embodiments of the present invention provide a method and apparatus for managing a distributed medical diagnostic imaging system. The distributed imaging system may include a plurality of subsystems, each subsystem of which may include a plurality of actors or task operators. The distributed imaging system may also include at least one configuration file providing information regarding components and/or capabilities of the distributed imaging system. The distributed imaging system may also include a subsystem communication channel for communication within the subsystem. The system includes a system manager for managing the distributed imaging system, within the distributed imaging system a subsystem manager for managing a subsystem and an actor or task operator executing certain functions under the instruction of the subsystem manager. The subsystem manager reports the results of each action to the system manager. The distributed imaging system includes a communications channel for transmitting data between the system manager and the subsystem. The system manager and subsystem manager may be implemented in hardware and/or in software.

The method includes transmitting a system command from a system manager to a subsystem manager that manages a subsystem to which the system command pertains. The subsystem manager relays the system command to an actor or task operator in the corresponding subsystem. Upon completion of the system command, the actor returns a task completion notification to the subsystem manager, and the subsystem manager relays the task completion notification to the system manager. When an error occurs during performance of a task, the actor returns an error message to the subsystem manager and the subsystem manager relays the error message to the system manager. Similarly, if an actor does not respond to the subsystem manager, the subsystem manager relays an error message to the system manager. The method may allow the location of errors in the system through communication and notification among the actor, subsystem manager, and system manager. The method may also allow scalability and adaptability in the system through "black box" system setup of subsystems and subsystem managers in relation to the system manager.

DETAILED DESCRIPTION OF THE INVENTION

Figure 1:
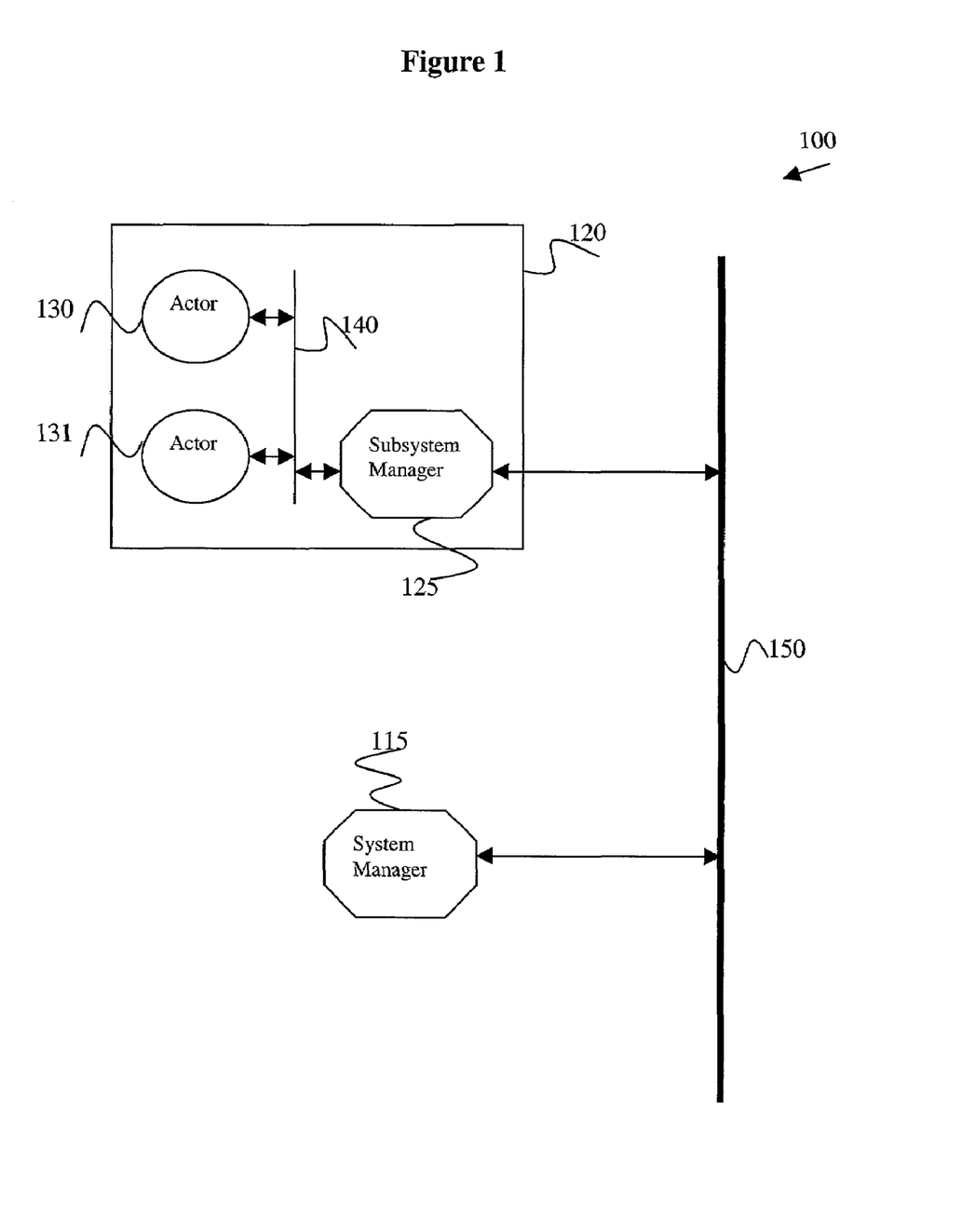
FIG. 1 illustrates a distributed medical diagnostic imaging system formed in accordance with an embodiment of the present invention.

FIG. 1 illustrates a medical diagnostic distributed imaging system 100, formed in accordance with an embodiment of the present invention. The distributed imaging system 100 includes a system manager 115, a subsystem 120, a subsystem manager 125, and a communication channel 150. While the distributed imaging system 100 is described with one subsystem 120, it will be understood that the system 100 may function with one or more subsystems. The subsystem 120 may include at least one actor. For purposes of illustration only, subsystem 120 includes a task operator or actor 130 and a task operator or actor 131. Medical diagnostic system components such as an x-ray detector, an x-ray emitter, and the like may be connected to the subsystem 120 and the actors 130-131.

The system 100 may be implemented as an Atlas™ medical diagnostic imaging system or any other medical diagnostic imaging system. The system 100 may be a system such as an x-ray imaging system, an ultrasound imaging system, a computed tomography imaging system, or other such medical diagnostic imaging system, for example. For illustrative purposes only, the system 100 will be described as an x-ray system.

The components of the system 100 may be housed in a single unit or may be housed in a plurality of separate units. For example, the components of an x-ray system (for example, x-ray source, detector, image acquisition unit, etc.) may be contained in a single piece of equipment. Alternatively, the x-ray system components may be housed in separate units, such as an x-ray emission unit located on one side of a target or patient, an x-ray detection unit located on another side of the target or patient, and an image acquisition computer receiving data from the x-ray detection unit, for example. The components of the system 100 may share the same location or may be remotely located from one another in a local area network. The components of the system 100 communicate with each other as described below.

The components of the system 100 communicate with each other using the communication channel 150. The communication channel 150 may be a bus, a cable, a fiber optic cable, the Internet, a private network, an infrared connection, a wireless connection, or other such communication connection. The communication channel 150 may be a combination of a communication connection and a software communication broker, for example. The components of the system 100 may communicate with each other over the communication channel 150 using a protocol such as Common Object Request Broker Architecture (CORBA) or other communication protocol. CORBA allows software to communicate with each other regardless of the location or design of the components. That is, differences between components may be transparent when using CORBA or other similar protocols to communicate. The components of the system 100 may also communicate over the communication channel 150 using a system-specific or custom communication protocol. Components, such as actors 130-131, within the subsystem 120 may communicate using a local communication channel 140, similar to the communication channel 150.

The system manager 115 and the subsystem manager 125 may be implemented in software and/or hardware. In the example of FIG. 1, the system manager 115 and the subsystem manager 125 are software modules running on different processor boards or different computers, for example. The subsystem 120 may be embodied in various processor boards, computers, or other components. The subsystem manager 125 may be located on the subsystem 120 components or may be located on separate boards or computers, for example. The system manager 115 may be located on any of the components of the system 100.

The system manager 115 may generate system or function commands to transmit to the subsystem manager 125 for execution by the actors 130-131 in the subsystem 120. System or function commands may include system boot, system shutdown, system reset at various levels, system power failure, system error handling, and the like. The system manager 115 transmits system commands to the subsystem manager 125 and receives an acknowledgement, status response, error, or other response from the subsystem manager 125.

The subsystem 120 may have different functional responsibilities (e.g., real-time acquisition controller, positioner, digital leader, for example), different hardware, and/or different operating systems (e.g., Windows NT, Vxworks, Linux, for example). The subsystem 120 includes various actors 130-131 that accomplish a functionality related to the subsystem's 120 role. The actors 130-131 are functional entities that may collaborate with each other to achieve a certain function or behavior. The actors 130-131 (or "task operators") represent system 100 or subsystem 120 functions. The actors 130-131 may be hardware, software, or a combination of hardware and software. The actors 130-131 may communicate over the communication channel 150 or the local communication channel 140 using Application Programming Interface (API) calls or other form of communication exchange, for example. API calls represent capabilities of the actors 130-131.

Several illustrative examples of actors are as follows. An image detector actor may convert an x-ray pattern resulting from the interaction of an x-ray beam with a patient into a usable information object called an image. An acquisition synchronizer actor may coordinate the actions of different actors 130-131 in the system 100. An emitter actor may control the emission of x-rays or another energy source through a target. A patient positioning actor may control the position of a patient in the system 100. A detector positioning actor may control the position of a detector in the system 100. An image correction actor may adjust an obtained image to correct for image artifacts and system offsets. A storage actor may store an obtained medical diagnostic image in digital form for later retrieval, analysis, or display, for example. Additionally, a display actor may display the medical diagnostic image on a monitor or other viewing device. In an ultrasound imaging system, a signal filter actor may filter the signals received back from a target. Also, an echo analysis actor may analyze the echoes sent back from a target to produce an image. A modulation actor may control amplitude and/or phase modulation of sound waves transmitted to a target to produce resulting echoes.

Figure 2:
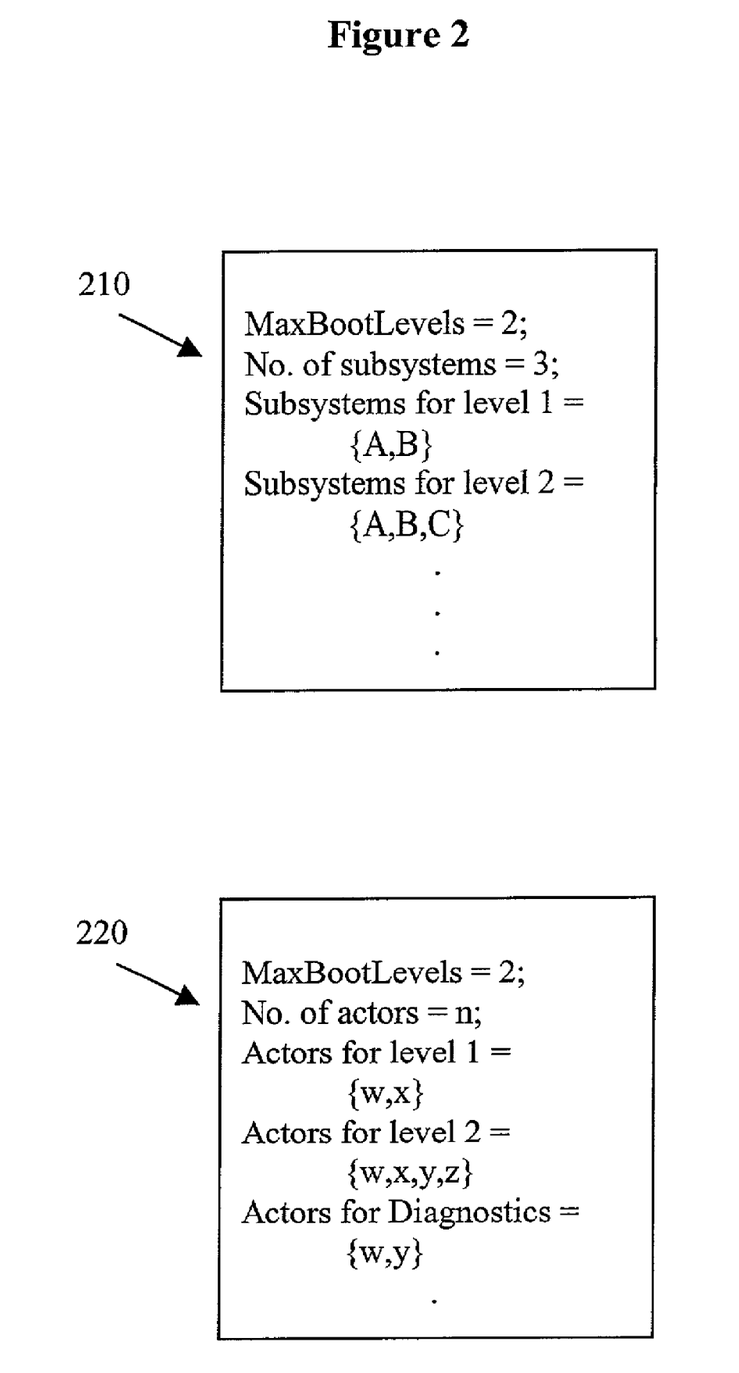
FIG. 2 illustrates configuration files used in accordance with an embodiment of the present invention.

FIG. 2 illustrates configuration files 210, 220 for the system 100 used in accordance with an embodiment of the present invention. The system 100 may include at least one configuration file 210 for the system manager 115 and at least one configuration file 220 for the subsystem manager 125. Alternatively, the system 100 may include a single configuration file 210 or 220 for both the system manager 115 and the subsystem manager 125. The configuration files 210, 220 may be used by the system manager 115 and/or the subsystem manager 125 to control and/or monitor the operation of the system 100, the subsystem 120, and the actors 130-131, for example. The configuration files 210, 220 may provide information regarding the composition and functionality of the system 100.

For example, the configuration file 220 for the subsystem manager 125 includes information regarding the number of actors 130-131 in the subsystem 120. The configuration file 220 for the subsystem manager 125 may also include the levels of operation and the phases within the level in which the subsystem 125 and the actors 130-131 may participate. Phases and levels are described below. For example, the configuration file 220 for the subsystem manager 125 includes the number of levels in the system boot or start-up operation in which the actors 130-131 may participate. For example, the configuration file 220 says the subsystem 120 has two levels (normal and EF, for example) in the boot operation. Actors w and x participate in level 1 (for example, the EF or emergency fluoro level) of system boot. Actors w, x, y, and z may participate in level 2 (for example, the normal operation level) of system boot. The configuration file 220 for the subsystem manager 125 may also include additional information, such as subsystem 120 and actor 130-131 timing information, diagnostic information, and the like.

The configuration file 210 for the system manager 115 is similar to configuration file 220, except the configuration file 210 relates to the system 100 and subsystem 120 rather than the subsystem 120 and the actors 130-131. The configuration file 210 for the system manager 115 includes information regarding the number of subsystems 120 in the system 100. The configuration file 210 may also include the levels of system operation, such as system boot, in which the subsystem 120 may participate.

Figure 3:
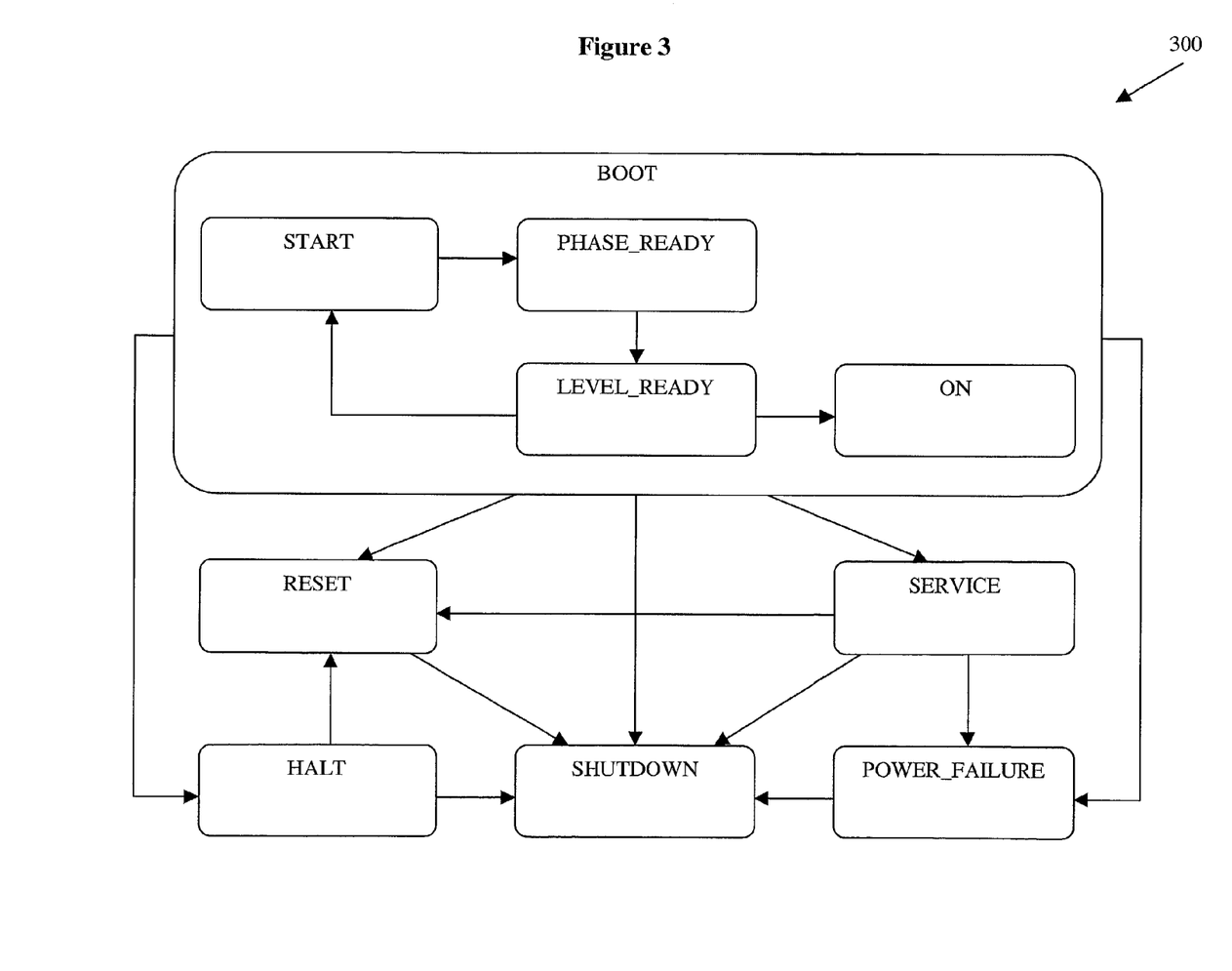
FIG. 3 illustrates a state transition diagram for system and subsystem managers used in accordance with an embodiment of the present invention.

The system manager 115 and the subsystem manager 125 may represent state machines that help coordinate the states of the system 100. The state machine(s) of the system 100 may include various states, such as boot, shutdown, power failure, and error handling, for example, that represent system 100 or subsystem 120 transitions upon various operations or activities, as shown in FIG. 3. States may include levels, such as emergency fluoro (EF) and normal, for example, representing modes of operation, and sub-levels or phases representing intermediate steps within each level.

For example, a system shutdown may be triggered. The system manager 115 may initiate a shutdown. The shutdown may be deliberate (such as by the push of a button or the flip of a switch, for example) or may be based on a system error, for example. If a human operator has triggered a reset, for example, of the system 100, the system manager 115 may direct the subsystem 125 to the reset phase and then transition to the shutdown phase for completion of the shutdown operation. The shutdown operation may also result automatically from an error in the system 100.

The following example illustrates how the system 100 operates during a system start-up or boot. As the system 100 is powered on (a process initiated by the push of a button, a key sequence, or the flip of a switch, for example), the subsystem 120 and the actors 130-131 within the subsystem 120 start the boot process. The subsystem manager 125 controls the boot operation for the subsystem 120, while the system manager 115 oversees the boot operation of the entire system 100. In order for the system 100 to boot, all components may traverse through levels that include multiple phases. Each level indicates a different state of readiness of the system 100. Each phase within a level indicates that a certain point of synchronization within the system 100 has been achieved to move forward in the boot activity.

At the start of a boot process, the actors 130-131 indicate to the subsystem manager 125 that the actors 130-131 are ready to go through the phases of boot. After the subsystem manager 125 is notified by the actors 130-131, the subsystem manager 125 notifies the system manager 115 that the subsystem 120 is ready for the boot process. The system manager 115 then instructs the subsystem manager 125 to initiate the next boot phase or level, as appropriate. When all of the boot levels and phases have been completed, the system manager 115 indicates that the system 100 is booted and ready for use.

For example, the boot operation may have phases zero, one, and two to reach the normal level of operation. As the actors 130-131 and the subsystem 120 complete each phase, a phase_ready signal is generated, signaling that the current phase is completed and execution may move to the next phase. When all appropriate phases have been completed and the normal level is reached, the level_ready signal is generated. The system 100 has completed the boot operation and is "on" for use by an operator.

If a problem arises or error occurs in the system 100 during a boot operation or other operation, the problem or error is simple to detect. Errors in the system 100 may be localized for easy detection and correction. For example, after the subsystem manager 125 receives the start command from the system manager 115, the subsystem manager 125 transmits the start command to the actors 130-131. The actors 130-131 attempt to execute the first phase of the start operation and transition to a phase_ready state. For example, the actor 130 and actor 131 may complete phase zero of the start phase and notify the subsystem manager 125 of the phase completion.

However, a hardware or software error may occur, for instance, in the actor 130 of the subsystem 120. In this example, the subsystem 120 would not receive a notice from actor 130 that the actor 130 is ready. When the subsystem manager 125 receives status reports from actor 131 but not actor 130, the subsystem manager 125 isolates the error in the actor 130. The subsystem manager 125 may then communicate to the system manager 115 that a problem has arisen in the actor 130. The system manager 115 may then notify an operator that an error has occurred in the actor 130. The system manager 115 may also record an error in a log file. Thus, for example, an x-ray technician may be informed that an error has occurred in the image detector actor and may concentrate diagnostic and repair efforts at the image detector.

The system 100 may also be reconfigured to accommodate additional subsystems and/or actors added to the system 100. Activity of the subsystem 120 is transparent to the system manager 115. Thus, changes within the subsystem 120 may be transparent to the operation of the system manager 115 and the system 100. Additionally, subsystems may be added and/or removed from the system 100 with notification by the subsystem's manager to the system manager 115.

Figure 4:
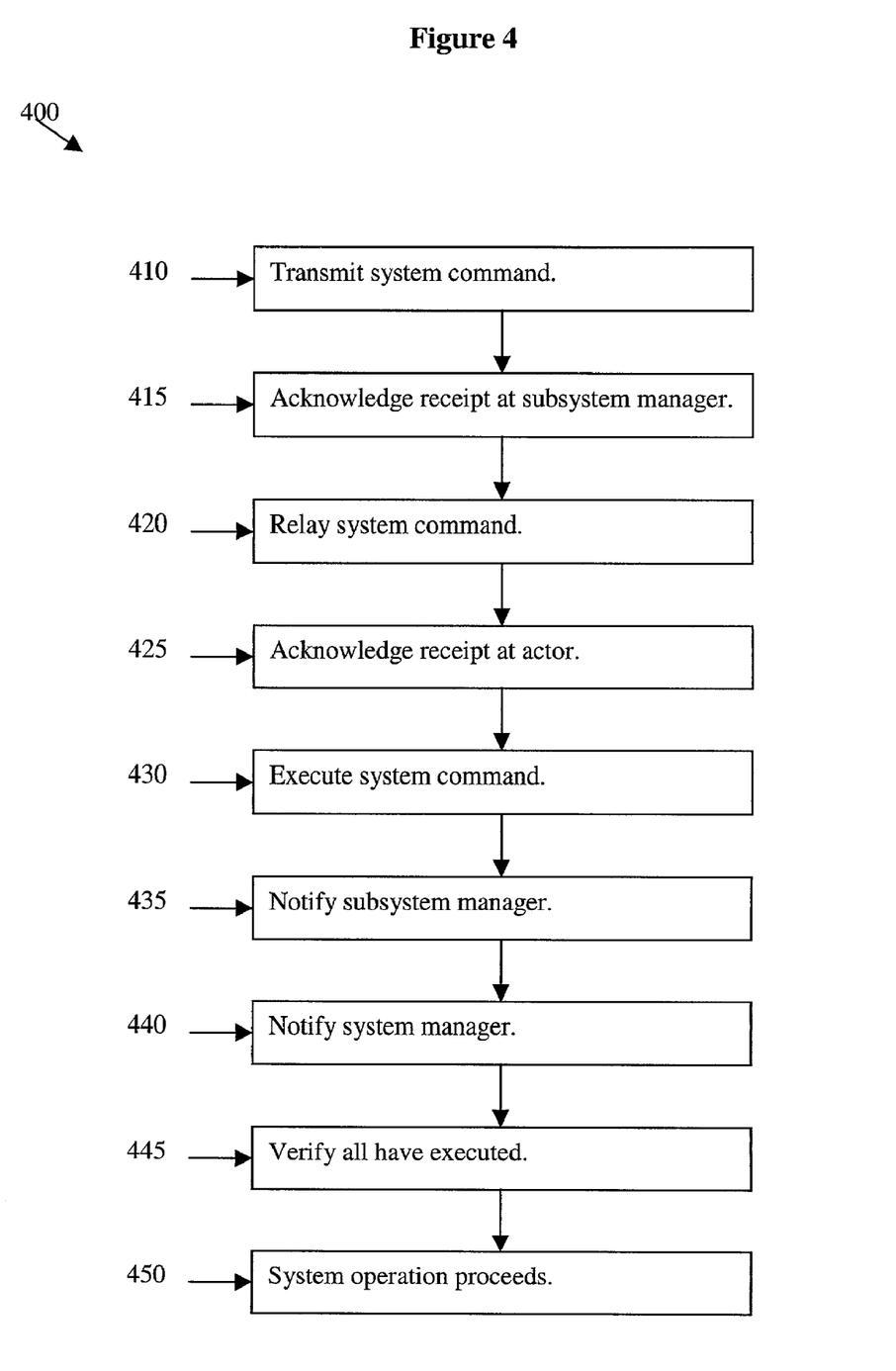
FIG. 4 illustrates a flow diagram for a method of generating and verifying commands in a distributed medical diagnostic imaging system in accordance with an embodiment of the present invention.

FIG. 4 illustrates a flow diagram 400 for a method of generating and verifying commands in a distributed medical diagnostic imaging system. First, at step 410, transmission of a system command occurs from a system manager 115 to at least one subsystem manager 125. The system manager 115 may use a system configuration file 210 to determine which subsystem manager(s) 125 receive the system command. The system command may be a command such as a boot command, a reset command, a shutdown command, a power failure command, an error handling command, or an operation command, for example. For example, the system manager 115 may send a system boot command to the subsystem managers 125 of an x-ray system. The subsystem managers(s) 125 manage individual subsystem(s) 120. The subsystems 120 may include task operators, or actors 130-131, that execute certain pre-defined functionalities. For the purposes of this example, a system 100 with a plurality of subsystems 120 including a plurality of actors 130-131 will be used for illustration purposes only. The subsystem manager(s) 125 may abstract or hide the specific configuration of the subsystem(s) 120 from other subsystem managers 125 and the system manager 115.

Next, at step 415, the subsystem managers 125 acknowledge the receipt of the system command from the system manager 115. For example, the subsystem managers 125 for the detector subsystem and image acquisition subsystem of an x-ray imaging system may acknowledge the receipt of a boot command from the x-ray system manager. Then, at step 420, the subsystem managers 125 relay the system command to the actors 130-131 in the respective subsystems 120. For example, the x-ray detector subsystem manager relays the boot command to the image detector actor in the subsystem. The subsystem manager 125 may use a subsystem configuration file 220 to determine which actors 130-131 in the subsystem 120 receive the system command. At step 425, the actors 130-131 acknowledge receipt of the system command. Next, at step 430, the actors 130-131 execute the system command. For example, the image detector actor completes the first phase of the boot operation.

At step 435, the actors 130-131 notify the respective subsystem managers 125 that the system command has been executed. At step 440, the subsystem managers 125 notify the system manager 115 that the system command has been executed. Then, at step 445, the system manager 115 may verify that the command has been executed by the subsystems 120. For example, the x-ray system manager may verify that all of the x-ray subsystems have executed a system boot operation. Finally, at step 450, system operation may proceed.

Figure 5:
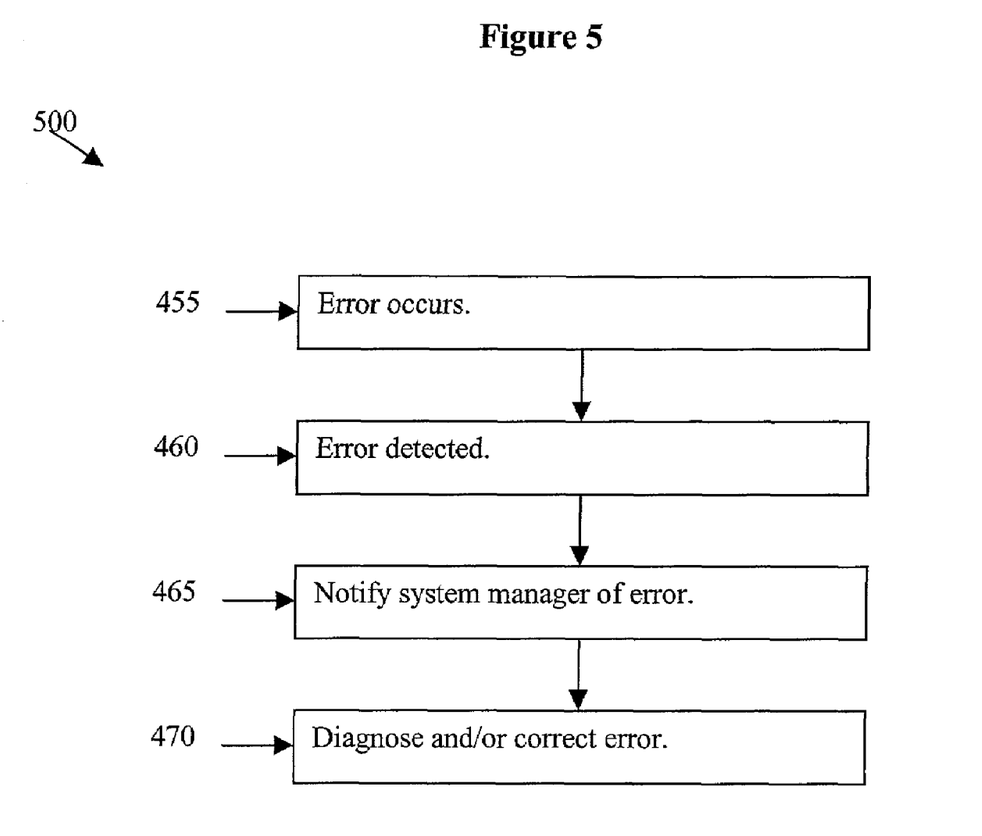
FIG. 5 illustrates a flow diagram for a method for detecting and isolating errors and faults that may occur during execution in a distributed medical diagnostic imaging system in accordance with an embodiment of the present invention.

FIG. 5 illustrates a flow chart for a method for detecting and isolating errors and faults that may occur during execution in a distributed imaging system. At step 455, an error occurs during the execution of a system command by an actor 130 in a subsystem 120. For example, an image detector actor may fail to shutdown properly in a detector subsystem of an x-ray system. That is, due to a malfunction, the image detector actor does not power down or shut off upon receipt of a shutdown command and does not reply to the detector subsystem manager. Then, at step 460, the failure of the actor 130 to execute and report back to the subsystem manager 125 is detected by the subsystem manager 125. For example, the detector subsystem receives no response from the image detector actor and flags an error at the image detector actor.

Next, at step 465, the subsystem manager 125 notifies the system manager 115 of the error that has occurred in the actor 130. For example, the detector subsystem manager transmits an error message to the x-ray system manager with information regarding the error that occurred, the subsystem 120 in which the error occurred, and the actor 130 in which the error occurred. At step 470, the system manager 115 may notify an operator of the error. The system manager 115 may generate a warning message or error log to alert an operator that an error has occurred in the actor 130 of the subsystem 120 and should be attended to.

Thus, an error in a medical diagnostic imaging system may be localized to a particular subsystem 120 or actor 130, and efforts may be concentrated at the location of the error. Additionally, messages passed from the failed component or the subsystem manager 125 supervising the failed component through the hierarchy of components to the system manager 115 may provide further information regarding the type of problem or details regarding the error.

Thus, certain embodiments provide a simplified method and system for management of a medical diagnostic imaging system through standardized system operation, such as boot, reset, shutdown, power failure, and error handling, for example. Additionally, certain embodiments provide system scalability by allowing addition of a subsystem without redesign of the system manager or of the boot, reset, shutdown, power failure, and error handling functions, for example. That is, a subsystem may be added to the system by modifying the system configuration file to reflect the presence of the new subsystem. Additionally, an actor, or task operator, may be added to a subsystem by modifying the subsystem configuration file to reflect the presence of the new actor. Similarly, an actor or subsystem may be removed from the system by removing the actor or subsystem from the appropriate configuration file. Thus, system scalability or growth/reduction may be accommodated through editing of configuration files or adaptability of system manager and/or subsystem manager programming without extensive modification or replacement of the system manager and/or subsystem manager in the reconfigured system.

Furthermore, certain embodiments allow improved testability of a system by allowing testing of boot, reset, shutdown, power failure, and/or error handling, for example, of subsystems without boot, reset, shutdown, power failure, or error handling of the entire system. Also, certain embodiments of the present invention may allow simplified system design and management by enabling management of subsystems without centralized knowledge of the composition of the subsystems. Certain embodiments may configure a system in hierarchical levels in order to manage the system. Certain embodiments of the present invention may synchronize system operation and allow a system to reach a state of uniform readiness.

Certain embodiments of the present invention model a medical diagnostic imaging system, the global states of the system, and transitions between the states. Certain embodiments of the present invention may model the system, system states, and state transitions in a "black box" model, regardless of the physical composition of the system across various types of medical diagnostic imaging systems. Certain embodiments of the present invention provide a common infrastructure that may be extended to many other types of medical equipment. Certain embodiments of the present invention may also model the operation of a medical diagnostic imaging system using an if/then/else model of operation or other system model. For example, system and subsystem managers may use status flags and "if" conditions to determine operation and synchronization of the system. For example, if a certain condition is met, then a flag is set and the process in question proceeds to the next condition.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A distributed medical diagnostic imaging system, comprising:
    a system manager generating, based on a system configuration file, function commands for at least one function from a set of functions including at least one of system boot, system reset, system shutdown, power failure, and error handling, said system configuration file including information regarding a number of subsystems in said system and levels within each of said at least one function which each of said subsystems participate;
    a subsystem capable of performing at least one function from said set of functions, said subsystem including at least one task operator capable of executing at least one task associated with each function performed by said subsystem; and
    a subsystem manager receiving said function commands and in response thereto providing, based on a subsystem configuration file, task instructions to said task operator concerning said at least one function, said task operator supplying task results regarding completion or failure of each of said task instructions to said subsystem manager, said subsystem manager transmitting function results regarding completion or failure of each of said function commands to said system manager based on said task results, said subsystem configuration file including a number of task operators in said subsystem and levels of operation within each of said at least one function in which said subsystem and said task operators participate.

2. The distributed medical diagnostic imaging system of claim 1, further comprising a plurality of subsystems and an equal plurality of subsystem managers.

3. The distributed medical diagnostic imaging system of claim 1, further comprising a plurality of subsystems connected to said system manager through a common communications channel.

4. The distributed medical diagnostic imaging system of claim 1, wherein said set of functions include at least one level.

5. The distributed medical diagnostic imaging system of claim 1, wherein said set of functions include at least one phase.

6. The distributed medical diagnostic imaging system of claim 1, wherein said system manager and said subsystem manager constitute state machines.

7. The distributed medical diagnostic imaging system of claim 1, wherein, when a failure occurs in a subsystem, said task operator generates data indicative of a level in a function at which said failure occurred.

8. The distributed medical diagnostic imaging system of claim 1, wherein, when a failure occurs in a subsystem, said task operator generates data indicative of a phase in a function at which said failure occurred.

9. The distributed medical diagnostic imaging system of claim 1, wherein, when a failure occurs in a subsystem, said subsystem manager generates data indicative of the subsystem at which said failure occurred.

10. The distributed medical diagnostic imaging system of claim 1, wherein, when a failure occurs in a task operator, said subsystem manager generates data indicative of the task operator at which said failure occurred.

11. A method for managing a distributed medical diagnostic imaging system, said method comprising:
    transmitting, based on a configuration file including information regarding a number of subsystems in said system and levels within at least one function in which each of said subsystems participate, a function command from a system manager to a subsystem manager for a subsystem; and
    relaying, based on said configuration file, said function command from said subsystem manager for said subsystem to a task operator for said subsystem, wherein said configuration file specifies levels within each of said at least one function in which said task operator participate.

12. The method of claim 11, further comprising receiving notification of completion of said function command from said task operator at said subsystem manager.

13. The method of claim 11, further comprising receiving notification of completion of said function command from said subsystem manager at said system manager.

14. The method of claim 11, further comprising receiving an error message from said task operator at said subsystem manager.

15. The method of claim 11, further comprising receiving an error message from said subsystem manager at said system manager.

16. The method of claim 11, further comprising a plurality of subsystems and an equal plurality of subsystem managers.

17. The method of claim 11, further comprising a plurality of task operators.

18. The method of claim 11, wherein said function command comprises at least one of booting, resetting, shutdown, power failure, and error handling.

19. The method of claim 11, wherein said task operator executes at least one task, including at least one of booting, resetting, error handling, and shutting down said subsystem.

20. A method for locating errors in a medical diagnostic imaging system, said method comprising:
    distributing control of said medical diagnostic imaging system among a plurality of hierarchical levels based on at least one configuration file, said plurality of hierarchical levels including a top level and a plurality of secondary levels;
    transmitting system commands from said top level to said plurality of secondary levels based on said at least one configuration file, said at least one configuration file including information regarding a number of secondary levels in said plurality of hierarchical levels and levels for execution of said system commands;
    flagging an error at at least one of said plurality of secondary levels; and
    receiving notification at said top level from said plurality of secondary levels, said notification comprising status of said plurality of secondary levels including said error at said at least one of said plurality of secondary levels.

* * * * *